US005565478A

United States Patent [19]
Kohn et al.

[11] Patent Number: 5,565,478
[45] Date of Patent: Oct. 15, 1996

[54] COMBINATION THERAPY USING SIGNAL TRANSDUCTION INHIBITORS WITH PACLITAXEL AND OTHER TAXANE ANALOGS

[75] Inventors: Elise C. Kohn, Olney; Eddie Reed, Germantown; Lance A. Liotta, Potomac, all of Md.

[73] Assignee: The United States of America as represented by the Department of Health & Human Services, Washington, D.C.

[21] Appl. No.: 212,612

[22] Filed: Mar. 14, 1994

[51] Int. Cl.$^6$ .................. A61K 31/41; A61K 31/415; A61K 31/335

[52] U.S. Cl. .............. 514/359; 514/8; 514/255; 514/383; 514/396; 514/399; 514/449

[58] Field of Search .................... 514/359, 396, 514/449, 399, 255, 383, 8

[56] References Cited

U.S. PATENT DOCUMENTS

| | | | |
|---|---|---|---|
| 3,717,655 | 2/1973 | Godefroi et al. | 260/309 |
| 4,144,346 | 3/1979 | Heeres et al. | 424/273 R |
| 4,223,036 | 9/1980 | Heeres et al. | 424/269 |
| 4,235,871 | 11/1980 | Papahadjopoulos et al. | 424/19 |
| 4,501,728 | 2/1985 | Geho et al. | 424/38 |
| 4,837,028 | 6/1989 | Allen | 424/450 |

OTHER PUBLICATIONS

Chabner, *Cancer Chemotherapy*, Lippencott, pp. 1–15 (1990).
DeVita, *Cancer, Principles & Practice of Oncology*, 3rd ed., Chapter 16, pp. 276–300, Lippencott, (1989).
Felder, et al., *J. Pharm. Exp. Therapy.*, 257:967–971 (1991).
Hupe, et al., *J. Biol. Chem.*, 266:10136–10142 (1991).
Kohn, et al., *J. Natl. Cancer Inst.*, 82:54–60 (1990).
Kohn, et al., *Cancer Research*, 52:3208–3212 (1992).
Kohn, et al., *Cancer Research*, 54:935–942 (1994).
Merritt, et al., *Biochem. J.*, 271:515–522 (1990).
Cole, et al., *Cancer and Metastasis Reviews*, 13:31–44 (1994).
Lin, et al., *Cell*, 72:269–278 (1993).
Gusovsky, et al., *J. Biol. Chem.*, 268:7768–7772 (1993).
Dinsmore, et al., *Cell*, 53:769–780 (1988).
Pirollet, et al., *Biochemistry*, 31:8849–8855 (1992).
Zamansky, et al., *J. Investigative Dermatology*, 97:985–994 (1991).
Holton, et al., *J. Am. Chem. Soc.*, 116:1597–1601 (1994).
Nicolaou, et al., *Nature*, 367:630–634 (1994).
Kumar, N., *J. Biol. Chem.*, 256:10435–10441 (1981).
Rowinsky, et al., *J. Natl. Cancer Inst.*, 82:1247–1259 (1990).
Schiff, et al., *Nature*, 277:665–667 (1979).
McGuire, et al., *Ann. Int. Med.*, 111:273–279 (1989).
Holmes, et al., *J. Natl. Cancer Inst.*, 83:1797–1805 (1991).
Kohn, et al., *J. Natl. Cancer Inst.*, 86:18–24 (1994).
Kohn, et al., *American Society for Clinical Oncology*, vol. 12, Abstract 814 (1993).
Szoka, et al., *Ann. Rev. Biophys. Bioeng.*, 9:467–508 (1980).
Hope, et al., *Chem. Phys. Lip.*, 40:89–107 (1986).
Holmes, et al., *J. Chromatography*, 613:317–325 (1993).
Sarosy, et al., *J. Clin. Oncol.*, 10:1165–1170 (1992).
Mason, *Am. J. Physiol.*, 264:C654–C662 (1993).

*Primary Examiner*—Marianne M. Cintins
*Assistant Examiner*—Phyllis G. Spivack
*Attorney, Agent, or Firm*—Townsend and Townsend and Crew

[57] ABSTRACT

The present invention provides compositions and methods for the treatment of cancer in a subject wherein compounds of formula I defined herein in combination with paclitaxel or other modified taxane analogs provide enhanced anticancer effects over the effects achieved with the individual compounds.

14 Claims, 5 Drawing Sheets

COMBINATION THERAPY USING SIGNAL TRANSDUCTION INHIBITORS WITH PACLITAXEL AND OTHER TAXANE ANALOGS

BACKGROUND OF THE INVENTION

The process of cancer progression, from normal cells to invasive and disseminated cells can be halted at many stages by therapeutic intervention. Combination therapy has been preferred for the treatment of most solid tumors as clinical trials suggested that there was improved disease-free survival and overall survival from the use of combination drug protocols. See Chabner, *Cancer Chemotherapy*, pp. 1–15, Lippencott; and DeVita, *Cancer, Principles & Practice of Oncology*, 3rd ed., pp 276–300, Lippencott. The basis for combination therapy may be either empiric, e.g. the use of several cytotoxic chemotherapeutic agents With potentially different mechanisms of action, or based upon laboratory demonstration of increased efficacy in vitro or in vivo.

Compound 1 is an inhibitor of calcium uptake through nonvoltage-gated and voltage-gated calcium channels. See. Felder, et al., *J. Pharm. Exp. Therap.*, 257:967–971 (1991); and Hupe, et al., *J. Biol. Chem.* 266:10136–10142 (1991). Compound 1 has demonstrated antiproliferative, anti-invasive, and anti-metastatic properties as a single agent both in vitro and in vivo. See Kohn, et al., *Proc. Natl. Acad. Sci. USA*, in press; co-pending application U.S. Ser. No. 08/123,614, now abandoned, and its CIP U.S. Ser. No. 08/209,651 filed Mar. 10, 1994; Kohn et al., *J. Natl. Cancer Inst.* 82:54–60 (1990); Kohn, et al., *Cancer Research*, 52:3208–3212 (1992); and Kohn, et al., *Cancer Research*, 54:935–942 (1994). Human clinical trials using compound 1 are now in progress.

Compound 2 is another agent with selectivity for receptor-mediated calcium entry (RMCE). This compound inhibits RMCE in platelets, endothelial cells and neutrophils, and blocks voltage-gated L-type calcium channels in vascular smooth muscle cells under patch clamp. Merritt, et al., *Biochem. J.* 271:515–522 (1990).

Modulation of calcium homeostasii may have many downstream effects within the cell, either from alteration of secondary signalling pathways or direct effects on calcium-sensitive events within the cell. See Cole, et al., *Cancer and Metastasis Reviews*, 13:31–44 (1994). Compound 1 has been shown to alter production of arachidonic acid, a calcium-sensitive event. See Felder, et al., *J. Pharm. Exp. Therap.* 257:967–971 (1991), Kohn, et al., *Cancer Research*, 54:935–942 (1994) and Lin, et al., *Cell* 72:269–278 (1993). Additionally, compound 1 inhibits phosphorylation events which are associated with receptor activation. See Kohn, et al., *Proc. Nat. Acad. Sci. USA* in press; co-pending application U.S. Ser. No. 08/123,614, now abandoned, and its CIP U.S. Ser. No. 08/209,651 filed Mar. 10, 1994; and Gusovsky, et al., *J. Biol. Chem.* 268:7768–7772 (1993). A direct effect of compound 1 may also be seen at steps such as microtubule polymerization and stabilization, due to its modulation of cellular calcium. See Dinsmore, et al., *Cell*, 53:769–780 (1988); Pirollet, et al., Biochemistry, 31:8849–8855 (1992); and Zamansky, et al., *J. Investigative Dermatology*, 97:985–994 (1991).

Paclitaxel (Taxol®), compound 3, is a diterpene isolated from the bark of the Western (Pacific) yew, *Taxus brevifolia* and is representative of a new class of therapeutic agent having a taxane ring system. Paclitaxel and its analogs have been produced by partial synthesis from 10-deacetylbaccatin III, a precursor obtained from yew needles and twigs, and by total synthesis. See Holton, et al., *J. Am. Chem. Soc.* 116:1597–1601 (1994) and Nicolaou, et al., *Nature* 367:630 (1994). Paclitaxel has been demonstrated to possess antineoplastic activity. More recently, it was shown that the antitumor activity of paclitaxel is due to a promotion of microtubule polymerization. See Kumar, N., *J. Biol. Chem.* 256:10435–10441 (1981); Rowinsky, et al., *J. Natl. Cancer Inst.*, 82:1247–1259 (1990); and Schiff, et al., *Nature*, 277:655–667 (1979). Paclitaxel has now demonstrated efficacy in several human tumors in clinical trials. See McGuire, et al., *Ann. Int. Med.*, 111:273–279 (1989); Holmes, et al., *J. Natl. Cancer Inst.*, 83:1797–1805 (1991); Kohn et al., J. Natl. Cancer Inst., 86:18–24 (1994); and Kohn, et al., *American Society for Clinical Oncology*, 12 (1993).

The role of signalling molecules and metal ions, specifically calcium, has previously been described for normal microtubule functioning. See Dinsmore, et al., *Cell*, 53:769–780 (1988); Pirollet, et al., Biochemistry, 31:8849–8855 (1992); and Zamansky, et al., Journal of Investigative Dermatology, 97:985–994 (1991). These observations suggest that low intracellular calcium might further stabilize microtubule polymerization.

SUMMARY OF THE INVENTION

It has now been discovered that enhanced anticancer effects are produced by the combination of certain chemotherapeutic agents with certain inhibitors of calcium influx.

In particular, modulation of intracellular calcium using inhibitors of calcium influx, such as compounds 1 and 2 and their analogs as well as the antimycotic imidazoles, augment the activity of chemotherapeutic agents such as paclitaxel (compound 3) and other modified taxane analogs. As a result, combination therapy is directed at all cancer conditions, especially solid tumors such as human ovarian cancer and human breast cancer.

DETAILED DESCRIPTION

The following abbreviations are used herein: DMSO, dimethyl sulfoxide; PEG-400, poly(ethylene glycol)-400; DMEM, Dulbecco's modified Eagle's medium; IMEM, Incomplete modified Eagle's medium; BSA, bovine serum albumin; EDTA, ethylenediamine tetraacetic acid; FCS, fetal calf serum; qod, every other day.

As used herein, the term "alkyl" refers to a saturated hydrocarbon radical which may be straight-chain or branched-chain (for example, ethyl, isopropyl, t-amyl, or 2,5-dimethylhexyl). Preferred alkyl groups are those containing 1 to 6 carbon atoms. All numerical ranges in this specification and claims are intended to be inclusive of their upper and lower limits.

The term "alkoxy" refers to an alkyl radical as described above which also bears an oxygen substituent which is capable of covalent attachment to another hydrocarbon radical (such as, for example, methoxy, ethoxy, phenoxy and t-butoxy).

The term "aromatic moieties" refers to a group of unsaturated cyclic hydrocarbons containing one or more rings. The rings are typified by benzene which has a 6-carbon ring containing three double bonds. Moieties containing multiple rings may have the rings fused together or linked covalently. Examples of such multiple ring aromatic moieties are naphthyl, biphenyl and anthracenyl. Any of the aromatic moieties described herein may be optionally substituted with halogen atoms, or other groups such as nitro, carboxyl, alkoxy and the like. In particular, the use of the term "halo-substituted phenyl" refers to a phenyl ring having one or more attached halogen atoms, for example, 4-chlorophenyl, 2,6-dichlorophenyl, 2-bromophenyl, 2,4-dibromophenyl, 3,5-difluorophenyl, and the like. The term "halo-substituted naphthyl" similarly refers to a naphthyl substituent having one or more attached halogen atoms, for example, 4-chloro-1-naphthyl, 4-chloro-2-naphthyl, 4,8-difluoro-1-naphthyl, and the like.

The term "alkoxyalkyl" refers to an alkoxy radical attached directly to an alkyl group. When used as a linking group, alkoxyalkyl refers to such radicals as —CH$_2$OCH$_2$—, —CH$_2$OCH$_2$CH$_2$—, —CH$_2$CH$_2$CH$_2$OCH$_2$— and —CH$_2$CH$_2$OCH$_2$CH$_2$—.

The term "antimycotic imidazoles" refers to those therapeutic agents having antimycotic activity and further having in common an imidazole ring. Examples of such antimycotic imidazoles are ketoconazole, miconazole, fluconazole, itraconazole and econazole.

The term "effective amount" refers to an amount sufficient to elicit the desired biological response.

The term "cancer" refers to all solid tumors, leukemias and lymphomas.

The term "supra-additive" when used to refer to an effect from a combination of agents, refers to a total effect which is greater than the sum of the effects due to each of the individual agents.

The term "subject" refers to any vertebrate species. Particularly preferred subjects are mammals, with humans being the most preferred subject. The term "patient" is used interchangeably with "subject".

In one aspect, the present invention provides pharmaceutical compositions which contain an effective amount of a compound of formula I and another effective amount of a second compound which is either paclitaxel, taxotere, or a modified taxane analog with a pharmaceutically acceptable carder.

$$Y\text{—}(CH_2)_p\text{-}Ar^1\text{-}X\text{—}Ar^2 \qquad (I)$$

For the compounds of formula I, the groups $Ar^1$ and $Ar^2$ are aromatic moieties and may be the same or different. Examples of aromatic moieties are phenyl, halo-substituted phenyl, naphthyl, and halo-substituted naphthyl.

The symbol X represents a linking group and may be O, S, SO$_2$, CO, CHCN, straight chain alkyl, alkoxy, and alkoxyalkyl.

The symbol Y represents a nitrogen-containing heterocyclic moiety of formula II:

in which A is N or CH; $R^1$ is hydrogen, —CONH$_2$ (carbamoyl), —CONHR$^3$, —CO$_2$H (carboxyl), —CO$_2$R$^3$, or —SO$_2$NH$_2$; $R^2$ is hydrogen, —NH$_2$ (amino), —NHCOC$_6$H$_5$ (benzamido), —NHCOR$^3$, —NHCHO (formamido), —NHR$^3$, or —N(R$^3$)$_2$ and $R^3$ is lower alkyl of from 1 to 6 carbon atoms. A preferred group for A is N. Preferred groups for $R^1$ are hydrogen, —CONH$_2$, —CONHR$^3$, and —CO$_2$H. Particularly preferred are —CONH$_2$ and —CO$_2$H. Preferred groups for $R^2$ are —NH$_2$, —NHCOC$_6$H$_5$, —NHCOR$^3$, and —NHR$^3$. Particularly preferred groups for $R^2$ are —NH$_2$ and —NHCOR$^3$.

The symbol p represents an integer of from 0 to 4.

In certain preferred embodiments, the compositions contain a compound of formula I in which Y is a radical of formula II, A is N and $R^1$ is —CONH$_2$.

In further preferred embodiments, the compositions contain a compound of formula I in which Y is a radical of formula II, A is N, $R^1$ is —CONH$_2$, and $R^2$ is —NH$_2$.

In still further preferred embodiments, the compositions contain a compound of formula I in which p is an integer of from 0 to 2, $A^1$ and $Ar^2$ are both halo-substituted phenyl, X is O, CO or CHCN, Y is a radical of formula II, A is N, $R^1$ is —$CONH_2$, and $R^2$ is —$NH_2$.

In the most preferred embodiment, the composition contains a compound of formula I in which p is 1, $Ar^1$ is 2,6-dichlorophenyl, $Ar^2$ is 4-chlorophenyl, X is CO, Y is a radical of formula II, A is N, $R^1$ is —$CONH_2$, and $R^2$ is —$NH_2$ (compound 1).

The second compound in the pharmaceutical composition is typically paclitaxel (Taxol®, compound 3), taxotere or a modified taxane analog. The modified taxane analogs are those compounds having a taxane ring bearing modified side chains. A number of these analogs have improved properties such as increased water solubility and stability. These analogs are known to those of skill in the art and are disclosed in U.S. Pat. Nos. 5,278,324; 5,272,171; 5,254,580; 5,250,683; 5,248,796; and 5,227,400, the disclosures of which are incorporated herein by reference. Taxotere can be prepared by the method in WO 9318210, the disclosure of which is incorporated herein by reference. In preferred embodiments, the second compound is paclitaxel or taxotere, more preferably paclitaxel.

In other embodiments, the compositions of the present invention can contain an antimycotic imidazole such as ketoconazole, miconazole, fluconazole, itraconazole and econazole.

The present invention further embraces pharmaceutical compositions containing a first compound associated with the modulation of calcium influx such as compound 2 and the related analogs described in co-pending application U.S. Ser. No. 07/985,402, now U.S. Pat. No. 5,359,078, together with a second compound which is paclitaxel (Taxol®, compound 3), taxotere or a modified taxane analog, in a pharmaceutically acceptable carrier. These compositions may optionally contain an antimycotic imidazole such as ketoconazole, miconazole, fluconazole, itraconazole and econazole.

The compounds used in the present inventive method are either commercially available or may be prepared using conventional synthetic techniques. Compound 1 can be prepared by the method described in U.S. Pat. No. 4,590,201. Briefly, 2,6-dichloro-4-methylbenzoic acid is converted to its corresponding benzoyl chloride using thionyl chloride in dimethylformamide. Reaction of this benzoyl chloride with chlorobenzene in the presence of aluminum trichloride provides 4-(4-chlorobenzoyl)-3,5-dichlorotoluene. Bromination of the methyl group is carried out using N-bromosuccinimide in the presence of catalytic amounts of dibenzoyl peroxide to provide 4-(4-chlorobenzoyl)-3,5-dichlorobenzyl bromide. The benzyl bromide is then converted to the corresponding benzyl azide using potassium azide. Treatment of the 4-(4-chlorobenzoyl)-3,5-dichlorobenzyl azide thus formed with 2-cyanoacetamide in the presence of sodium methoxide provides after workup, 5-amino-1-(4-(4-chlorobenzoyl)-3,5-dichlorobenzyl)- 1,2,3-triazole-4-carboxamide (Compound 1).

Related analogs can be prepared either by derivatization of compound 1 or by the general approach used for compound 1. Materials and conditions will vary depending on the desired analog. Particular conditions are known to those of skill in the art.

Antimycotic imidazoles, such as ketoconazole, econazole and miconazole are either available from Janssen Pharmaceutica, Inc. (Piscataway, N.J., USA) or may be prepared by procedures outlined in U.S Pat. Nos. 3,717,655, 4,144,346 and 4,223,036, the disclosures of which are incorporated herein by reference.

The pharmaceutical compositions of the present invention will also contain a pharmaceutically acceptable carrier. Pharmaceutically acceptable carriers are well known to those who are skilled in the art. The choice of a carrier will be determined in part by the particular compounds, as well as by the particular method used to administer the composition. Accordingly, there is a wide variety of suitable formulations of the pharmaceutical compositions of the present invention. Some of the carriers used in these formulations include water, saline and PEG 400 (for oral administration); propellants such as dichlorodifluoromethane, propane or nitrogen (for inhalation administration); natural or synthetic triglycerides or paraffin hydrocarbons (for suppository bases for rectal administration); and aqueous or non-aqueous isotonic sterile injection solutions, such as Cremophor EL, (for intravenous, intramuscular, intradermal, intraperitoneal, and subcutaneous administration). Additionally, the formulations may contain detergents, such as Tween 80.

The compounds and compositions of the present invention may also be administered encapsulated in liposomes, pharmaceutical delivery vehicles wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomycelin, steroids such as cholesterol, more or less ionic surfactants such as dicetylphosphate, stearylamine, or phosphatidic acid, and/or other materials of a hydrophobic nature. The diameters of the liposomes generally range from about 15 nm to about 5 microns.

A variety of methods are available for preparing liposomes as described in, e.g., Szoka et al., *Ann. Rev. Biophys. Bioeng.* 9:467 (1980), U.S. Pat. Nos. 4,235,871, 4,501,728, 4,837,028, the text Liposomes, Marc J.Ostro, ed., Chapter 1, Marcel Dekker, Inc., New York (1983), and Hope, et al., *Chem. Phys. Lip.* 40:89 (1986), all of which are incorporated herein by reference.

In another aspect, the present invention provides a method for treating cancer in a subject. In this method, the treatment involves a first step of administering to a subject an effective amount of a first compound of formula I and administering to the subject a second compound which is paclitaxel, taxotere or a modified taxane analog.

For the compounds of formula I, the groups $Ar^1$ and $Ar^2$ are aromatic moieties and may be the same or different. Examples of aromatic moieties are phenyl, halo-substituted phenyl, naphthyl, and halo-substituted naphthyl.

The symbol X represents a linking group and may be O, S, $SO_2$, CO, CHCN, straight chain alkyl, alkoxy, and alkoxyalkyl.

The symbol Y represents a nitrogen-containing heterocyclic moiety of formula II:

in which A is N or CH; $R^1$ is hydrogen, —$CONH_2$ (carbamoyl), —$CONHR^3$, —$CO_2H$ (carboxyl), —$CO_2R^3$, or —$SO_2NH_2$; $R^2$ is hydrogen, —$NH_2$ (amino), —$NHCOC_6H_5$ (benzamido), —$NHCOR^3$, —NHCHO (formamido), —$NHR^3$, or —$N(R^3)_2$ and $R^3$ is lower alkyl of from 1 to 6 carbon atoms. A preferred group for A is N. Preferred groups for $R^1$ are hydrogen, —$CONH_2$, —$CONHR^3$, and —$CO_2H$. Particularly preferred are —$CONH_2$ and —$CO_2H$. Preferred groups for $R^2$ are —$NH_2$, —$NHCOC_6H_5$, —$NHCOR^3$, and —$NHR^3$. Particularly preferred groups for $R^2$ are —$NH_2$ and —$NHCOR^3$.

The symbol p represents an integer of from 0 to 4.

In certain preferred embodiments, this method uses a compound of formula I in which Y is a radical of formula II, A is N and $R^1$ is —$CONH_2$.

In further preferred embodiments, this method uses a compound of formula I in which Y is a radical of formula II, A is N, $R^1$ is —$CONH_2$, and $R^2$ is —$NH_2$.

In still further preferred embodiments, this method uses a compound of formula I in which p is an integer of from 0 to 2, $Ar^1$ and $Ar^2$ are both halo-substituted phenyl, X is O, CO or CHCN, Y is a radical of formula II, A is N, $R^1$ is —$CONH_2$, and $R^2$ is —$NH_2$.

In the most preferred embodiment, this method uses a compound of formula I in which p is 1, $Ar^1$ is 2,6-dichlorophenyl, $Ar^2$ is 4-chlorophenyl, X is CO, Y is a radical of formula II, A is N, $R^1$ is —$CONH_2$, and $R^2$ is —$NH_2$ (compound 1).

The second compound of the present inventive method is paclitaxel, taxotere or a modified taxane analog, preferably paclitaxel or taxotere, and most preferably paclitaxel.

The two compounds are administered in combination according to the invention. The term "in combination" in this context means that the drugs are given contemporaneously, either simultaneously or sequentially. If given sequentially, one of the two compounds is preferably detectable in the serum of the subject at the onset of administration of the other compound. Preferably, a compound of formula I is administered first, followed by administration the second compound, preferably paclitaxel. More preferably, paclitaxel is administered about two hours after a compound of formula I. Alternatively, the first compound and the second compound can be given simultaneously, or the second compound could be given first, followed by a compound of formula I.

In preferred embodiments, the effective amount of the first compound is from about 50 mg/m² to about 500 mg/m² of body surface area of the subject and the effective amount of the second compound is from about 75 mg/m² to about 300 mg/m² of body surface area of the subject. Preferably the subject is human.

In a particularly preferred embodiment of the present inventive method, the subject is human, the first compound is compound 1 and the second compound is paclitaxel (compound 3).

In other preferred embodiments, the first compound is administered orally and the second compound is administered by intravenous injection.

In yet another group of preferred embodiments, the compound of steps (i) and (ii) are administered in combination with G-CSF, an antimycotic imidazole, or a combination thereof.

In still another group of preferred embodiments, the method is used to treat a cancer which is breast cancer, ovarian cancer, colon cancer and lung cancer, prostate cancer, bladder cancer, melanoma or Kaposi's sarcoma.

The present invention further embraces the methods described above, wherein the first compound of formula I is replaced with compound 2 and its related analogs described in co-pending application U.S. Ser. No. 07/985,402, now U.S. Pat. No. 5,359,078, the disclosure of which is incorporated herein by reference.

A schedule dependence of the combination of compound 1 and paclitaxel was demonstrated with the invention. These data suggest that attainable plasma levels of compound 1 (1–5 µM) can potentiate the effects of paclitaxel in patients with cancer. A fixed dose of compound 1 at 100 mg/m²/d can yield plasma levels in humans of at least 1–5 µM by the 8th day of administration and caused no significant toxicity. See, co-pending application U.S. Ser. No. 07/985,402, now U.S. Pat. No. 5,359,078, and Holmes, et al., *J. Chromatography* 613:317–325 (1993).

Compound 1 can be formulated into any of a number of preparations for oral, parenteral, and topical usage. Preferably, compound 1 is administered orally. A preferred formulation is a compound 1 solution in polyethelene glycol, typically of about 400 molecular weight (PEG-400). Compound I can be presented in other formulations, such as a gel cap containing compound 1 in PEG-400 or as a micronized powder in capsules.

Compound 1 in PEG-400 solution is administered daily in a single dose, in divided doses during the course of a day, or in a single dose every other day. Preferably, it is administered daily in a single dose. The initial dosage is usually about 100–200 milligrams per meter squared per day (mg/m²/qd). An alternative schedule is up to 330 mg/m²/every other day (qod).

The dosage is usually increased until a dose limiting toxicity is encountered. For example, a dose limiting toxicity could be neutropenia, sensory peripheral neuropathy, nausea and emesis.

Typically, patients at the 100 mg/m²/day dosing level experience no significant toxicity, and achieve plasma compound 1 concentrations of 1–5 micromolar (µM) or greater by the 8th day of therapy. Usual plasma levels at this dose show a plateau of 3–4 µg/mL (5–10 µM).

More generally, for oral administration, compounds of formula I can be administered at a dose of up to 3000 mg/m² body surface area, which approximates 6 grams/day in the average patient. This can be accomplished via single or divided doses. For intravenous administration, such compounds can be administered at the dose of up to about 2500 mg/m²/d. For intravesicle administration, such compounds can be administered at the dose of up to about 2500 mg/m²/d. For topical administration, the dose can be up to about 2500 mg/m²/d. The dose for inhalation/aerosol administration can be up to about 2500 mg/m²/d. Direct intraperitoneal administration can be performed using up to about 3000 mg/m²/d. The dose for reservoir administration to the brain or spinal fluid can be up to about 2000 mg/m²/d. For slow release intraperitoneal or subcutaneous administration, the dose can be up to about 10 g/day in a bolus. For intrathecal administration, the dose can be up to about 2000 mg/m²/d.

Compound 1 (NSC 609974) is available from the National Cancer Institute as a white powder. Preferably, it is dispensed as a 100 mg/mL solution in PEG-400. Compound 1 in PEG-400 solution is stable for at least 3 months at temperatures of up to 50° C. It is administered as a measured liquid dose daily for 8 days or more. It is recommended that patients take nothing by mouth for 3 hours prior to and 1 hour after taking the compound 1.

Common low-grade toxicities of compound 1 included nausea and emesis. Uncommon toxicities include mood changes (low-grade), peripheral neuropathy (mild to moderate) and neutropenia. Toxicities of paclitaxel include nausea, emesis, diarrhea, neutropenia, thrombocytopenia, anemia, hair loss, myalgia, cardiac conduction abnormalities, hypersensitivity reactions, peripheral and autonomic neuropathy, mucositis.

Paclitaxel can be given in a dose of less than or equal to about 110 mg/m$^2$ up to 300 mg/m$^2$ over 3–24 hours every 21 days, or more. A dose limiting toxicity of peripheral neuropathy has been seen above 300 mg/m$^2$. The administration of granulocyte colony-stimulating factor (G-CSF, discussed below) can enable paclitaxel levels of 250 mg/m$^2$ to be administered without treatment delay and without unacceptable toxicity.

Paclitaxel is available from Bristol-Myers Squibb (Princeton, N.J., USA) as a concentrated non-aqueous solution of 6 mg/mL in 5 mL ampules (30 mg/ampule) in a vehicle of polyoxyethylated castor oil (Cremophor EL) 50% and dehydrated alcohol 50%. The intact ampules can be stored under refrigeration and are diluted just before use.

Paclitaxel can be administered on a outpatient basis as a 3 hour intravenous infusion beginning about 2 hours after the eighth compound 1 dose.

Paclitaxel can be prepared by diluting the dose in a crystalloid solution, such as 0.9% sodium chloride injectable, 5% dextrose injectable, 5% dextrose in combination with 0.9% sodium chloride injectable, or 5% Ringers solution, to a final concentration of 0.3 to 1.3 mg/mL.

Paclitaxel must be prepared in glass, polypropylene or polyolefin containers due to leaching of diethylhexphtyalate (DEHP) plasticizer from polyvinylchloride (PVC) bags and intravenous tubing by the Cremophor vehicle in which the paclitaxel is solubilized. Each bag or bottle should be prepared immediately before administration.

A suggested appropriate schedule using compound I and paclitaxel according to the invention is as follows. Compound 1 is given for each of 8 consecutive days. On the 8th day paclitaxel is administered. G-CSF may be administered starting on the 9th day where indicated and continuing to the 18th day if needed. One cycle of therapy is counted from the first day of compound 1 administration and for a total of 21 days. Thus a second cycle of therapy may begin on the 22rid day. Escalation may proceed after successful completion of a first cycle (21 days) at a given level of therapy. The compound 1 may be held constant at, for example, 100 mg/m$^2$/day. in such a case, an example of paclitaxel dose escalation is as follows: a starting dose of 110 mg/m$^2$ is increased to 135, 170, 200 and 250.

Premedication for the paclitaxel infusion is recommended and can include treatment with asteroid, generally a glucocorticoid, to help avoid hypersensitivity reactions. An example is hydrocortisone 100 mg by mouth at 12 hours and 6 hours immediately prior to paclitaxel administration. An antihistamine, such as diphenhydramine or hydroxyzine, and an H2 blocker, such as cimetidine or ranitidine, are recommended adjuncts to paclitaxel therapy. For example, diphenhydramine at 50 milligrams by mouth or intravenously and cimetidine 300 mg by mouth or intravenously 30 minutes prior to paclitaxel administration can be given.

Drugs which are well known to the practitioner, such as metaclopromide and prochlorperazine, may be use to premedicate or to treat the patient for nausea or emesis as needed.

G-CSF (Neupogen®) is a cytokine which blunts paclitaxel-induced neutropenia. See, Sarosy, et al., *J. Clin. Oncol.* 10:1165–1170 (1992). G-CSF can be given in a flexible dosing fashion to ensure that maximal doses of paclitaxel are administered. That is, if a patient develops fever and neutropenia while on a therapy of the invention, the next cycle of therapy can include G-CSF, or an increased dose of G-CSF, with maintenance of the anti-cancer medications.

The starting dose of G-CSF is 5 μg/kg/day with escalation to 10, 15 and 20 or more μg/kg/day. Escalation of the G-CSF dose is performed as indicated according to the judgement and experience of the clinical practitioner. Escalation of G-CSF up to 30 μg/kg/d is associated with maintenance of the dose of paclitaxel, either alone or in combination with compound 1. G-CSF is available as a recombinant cytokine from Amgen (Thousand Oaks, Calif., USA). It is typically administered by subcutaneous injection.

Antimycotic imidazoles, such as ketoconazole, fluconazole, itraconazole, econazole and miconazole, are also known to effect calcium levels in cells. See, Mason, *Am. J. Physiol.* 264:C654–C662 (1993). These antimycotic imidazoles can be given in combination with therapeutics of the invention. In particular, ketoconazole has been shown to augment the activity of paclitaxel in vitro, and it can cause a two-fold increase in circulating levels of paclitaxel. An appropriate dose and schedule for ketoconazole in this context is 200 mg orally, two hours prior to initiation of the paclitaxel infusion.

In evaluating the patient, both before and during therapy, it is recommended that the practitioner obtain a history, physical examination and laboratory studies at the beginning of the therapy and at intervals thereafter as indicated. A careful neurological examination should be performed. A complete laboratory panel including a complete blood count, an automated series of chemistries, platelet count, magnesium, amylase, protime, partial thromboplastin time, erythrocyte sedimentation rate, thyroid function tests, and tumor markers as appropriate to the malignancy (e.g. CA-125, CEA, PSA).

The automated chemistries are well known to those of skill in the art and can include levels of electrolytes (e.g., sodium, potassium, chlorides, and carbon dioxide), cholesterol, glucose, triglycerides, lipids, calcium, phosphorus, creatinine, blood-urea-nitrogen, and enzymes such as alkaline phosphatase, lactose dehydrogenase (LDH), serum transaminases (such as SCOT, SGPT, GGT), creatine phosphokinases (CPK). Additionally, a chest X-ray and electrocardiogram (EKG) should be obtained. Also recommended is a urine analysis, a 24 hour creatinine clearance, and measurements of radiographic or physical examination documentation of evaluable disease.

Patients can attain complete resolution of the disease. These patients may receive an additional two cycles of therapy as long as the additional therapy is not unduly complicated by side effects. Patients may have a partial response or maintain a stable disease state. Such patients may continue on therapy until a complete response is obtained, until the disease breaks through the therapy, or until unacceptable toxicity occurs. Patients with progressive disease or unacceptable toxicity are generally removed from therapy with the invention.

Clinical evaluation during therapy and afterwards is recommended. Such evaluation includes complete history and physical examinations with emphasis on careful neurological examination. Laboratory parameters should be followed as noted above. Particular attention should be paid to complete blood counts, platelet counts, white count differentials and automated chemical profiles and clinical markers as discussed above. Chest X-rays and EKGs can be obtained periodically, such as every other treatment cycle. At least the complete blood count with differential and platelet count should be checked about twice a week.

Dosage modifications are made at the discretion of the practitioner. Hematopoietic dose limiting toxicity may be manifest by episodes of fever in the face of neutropenia. Thrombocytopenia may require transfusions and downward dosage adjustment. Persistent transfusion-dependent anemia requires dosages adjustment or discontinuation of therapy. Objective evidence of neuropathy can be corroborated with electromyographic studies and nerve conduction studies. Dosage modification may be indicated. Analysis of therapeutic levels can be performed. Compound I and paclitaxel can be detected and quantified in patient fluids, such as blood or serum, by reverse phase high performance liquid chromatography (HPLC).

Fluid or tissue samples may be obtained. For example ascites or pleural fluids may be sampled for diagnostic or therapeutic reasons. Tissue biopsy samples may be helpful to evaluate therapy.

Alternatives to the embodiments described above include administration in any suitable manner, preferably with pharmaceutically acceptable carriers. One skilled in the art will appreciate that suitable methods of administering such compounds in the context of the present invention to an animal are available, and, although more than one route can be used to administer a particular compound, a particular route can provide a more immediate and more effective reaction than another route. Pharmaceutically acceptable carriers are also well-known to those who are skilled in the art. The choice of carrier will be determined in part by the particular compound, as well as by the particular method used to administer the composition. Accordingly, there is a wide variety of suitable formulations of the pharmaceutical composition of the present invention. Formulations and methods of administration are well known to those skilled in the art and can be found in *Remington's Pharmaceutical Sciences* 17th ed., Mack Publishing Co., Easton, Pa. (1985).

Formulations suitable for oral administration can consist of (a) liquid solutions, such as an effective amount of the compound dissolved in diluents, such as water, saline or PEG 400; (b) capsules, sachets or tablets, each containing a predetermined amount of the active ingredient, as solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium sterate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such as carriers as are known in the art.

The active ingredients, alone or in combination with other suitable components, can be made into aerosol formulations to be administered via inhalation or local application to mucous membranes such as those of the mouth and nasal passages, and topically to the skin. These aerosol formulations can be placed into pressurized acceptable propellants, such as dichlorodifluoromethane, propane, nitrogen, and the like.

Suitable formulations for rectal administration include, for example, suppositories, which consist of the active ingredient with a suppository base. Suitable suppository bases include natural or synthetic triglycerides or paraffin hydrocarbons. In addition, it is also possible to use gelatin rectal capsules which consist of a combination of the active ingredient with a base, such as, for example, liquid triglycerides, polyethylene glycols, and paraffin hydrocarbons.

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, detergents, and solutes that render the formulation isotonic with the blood of the intended recipient, for example Cremophor, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiting only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compound employed and the condition of the animal, as well as the body weight or surface area of the animal to be treated. The size of the dose also will be determined by the existence, nature, and extent of any adverse side-effects that might accompany the administration of a particular compound in a particular animal. In determining the effective amount of the active ingredient to be administered in the treatment or prophylaxis of cancer treatment, the physician needs to evaluate circulating plasma levels, toxicities, and tumor growth inhibition, and evidence of cancer progression.

In the practice of this invention, the compounds can be administered, for example, by intravenous infusion, orally, topically, intraperitoneally, intravesically or intrathecally for treatment of lymphomas, leukemias, and all solid tumors. The compounds could be applied in a suitable vehicle for the local and topical treatment of cancer. Tumors such as basal cell carcinoma and Kaposi's sarcoma could be treated by topical administration of the agents taught herein. Prevention of tumor recurrence by administration of the composition in a manner intended to reach the particular site where such cells are proliferating would be most advantageous. For example, intraperitoneal administration would be a means of treating tumors known to cause peritoneal carcinomatosis. Intravesical treatment of transitional cell carcinoma and topical treatment of mycosis fungoides are further examples of site-directed treatment. Systemic administration may be accomplished by continuous infusion, bolus parenteral treatment, or release from an implanted slow release depot. It is obvious that this method can supplement treatment of cancer by any conventional therapy including cytotoxic agents and biologic response modifiers. The method disclosed may be used in any malignancy as a means of treatment to prevent the transition from in situ to invasive carcinoma or invasive to metastatic carcinoma.

The methods taught herein are not restricted to use in treatment of malignancies but may be extended to the treatment of infectious diseases and diseases related to angiogenesis. See co-pending application U.S. Ser. No. 08/123,614, now abandoned, and its CIP, co-pending application U.S. Ser. No. 08/209,651 (filed Mar. 10, 1994) the disclosures of which are incorporated herein by reference. Disease conditions such as endometriosis, psoriasis, and eczema which result from localized spread of diseased cells may also be advantageously treated. Additionally, disease states which rely on aberrant signal transduction/proliferation may also be treated. See co-pending application U.S. Ser. No. 07/985,402, incorporated herein by reference. Diseases of potentially aberrant signal transduction/proliferation may include the collagen vasculitides (i.e., systemic lupus erthythematosis and rheumatoid arthritis), neurologic diseases (i.e., dementia and nerve conduction diseases), diseases of transport (i.e., cystic fibrosis), toxic effects of agents (i.e., cisplatin-related neuropathy), and cellular dysfunction (i.e., myelodysfunction syndromes). See also, co-pending U.S. Ser. No. 08/122,277, abandoned, and its CIP, co-pending application U.S. Ser. No. 08/209,651, filed Mar. 10, 1994, the disclosures of which are incorporated herein by reference.

The following experiments are provided by way of example and not by way of limitation.

EXAMPLES

Materials

Compound 1 was supplied as a powder by the Developmental Therapeutics Program of the National Cancer Institute. A 20 μM stock solution was made in DMSO or PEG-400, and aliquots were stored at −70° C. For use, a 10 μM solution was prepared daily in media (DMEM), and serial dilutions were made as needed. Paclitaxel was supplied by the Pharmaceuticals Resource Branch of the Cancer Therapy Evaluation Program of the National Cancer Institute and is commercially available as Taxol® from Sigma Chemical Company (St. Louis, Miss., USA) and Bristol-Myers Squibb (Princeton, N.J., USA). Paclitaxel was solubilized in DMSO and stored at −70° C. until needed. Dilutions were made just prior to use. Carboplatin is available from Sigma Chemical Co. (St. Louis, Miss., USA).

Cell Cultures

A2780 human ovarian cancer cells are available from the ATCC. The cells were cultured in RPMI 1640 with 10% FCS under standard conditions. See the ATCC catalog. The culture media contained penicillin and streptomycin and in some instances, insulin.

A2780-CP70 are a selected subline of A2780 which are stably resistant to cisplatin in the absence of continuous exposure. These cells were obtained from Robert Ozols, MD at the Fox Chase Cancer Center, Philadelphia, Pa., USA. These cells were cultured as described above.

MDA-231 hormone-resistant human breast cancer cells from ATCC were cultured in DMEM with 10% FCS and penicillin/streptomycin, under standard conditions.

EXAMPLE 1

This example illustrates the dose determination to achieve $IC_{50}$ values for compound 1 and paclitaxel (compound 3) in treatment of A2780 and A2780-CP70 cells.

Figure 1:
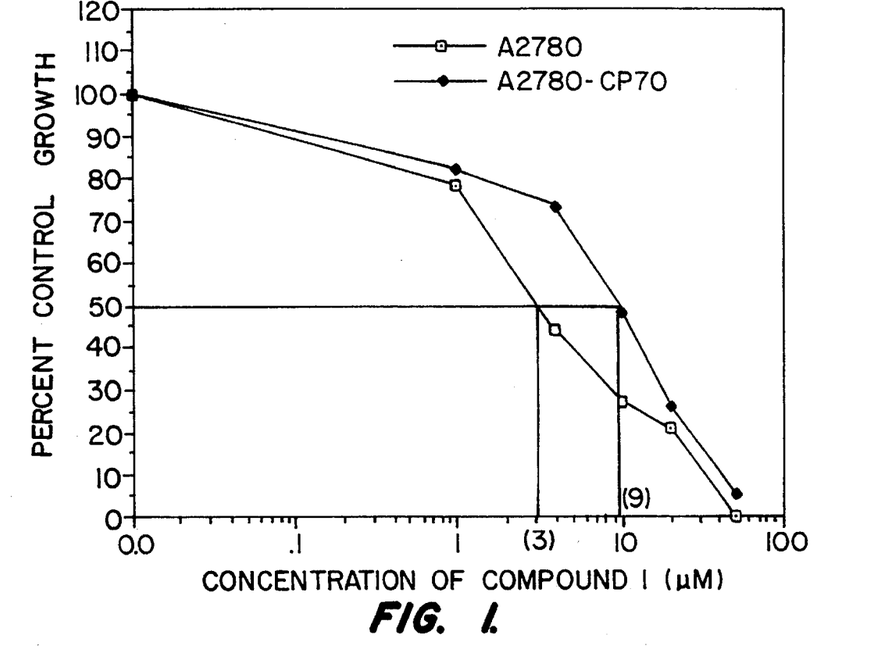
FIG. 1 shows the inhibition of human ovarian cancer cell growth using compound 1. Values of $IC_{50}$ are shown for both A2780 cells and A2780-CP70 cells (cisplatin-resistant).

Cells (500) were plated in 6-well plates and allowed to grow overnight. Compound 1 (0 to 30 μM) or paclitaxel (0 to 0.01/μM) in complete media was added to the wells after washing with PBS. Controls were conducted by adding DMSO vehicle in complete media. After a 24 hr exposure to either compounds 1, 3 or control, the cells were washed with PBS and refed with serum-containing complete media. After 5 days of incubation, the cells were washed once with PBS and then stained with methylene blue in 40% methanol for 20 min. The wells were rinsed gently with water and allowed to air dry. Colonies were counted by hand. The results for compound 1 are presented in FIG. 1. The $IC_{50}$ for compound 1 was found to be 3 μM for A2780 cells and 9.5 μM for A2780-CP70 cells.

EXAMPLE 2

This example illustrates the effect of treating cells with compound 1 and a subsequent treatment with compound 3.

Figure 2:
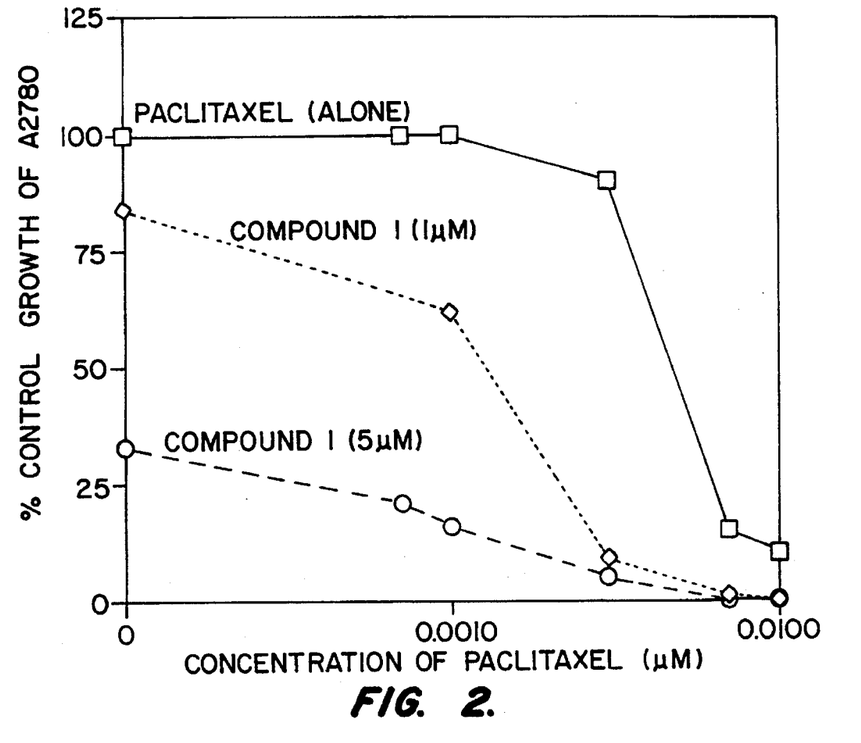
FIG. 2 shows the effect of treating A2780 cells with compound 1 (at 0, 1 and 5 μM) followed by paclitaxel.
Figure 3:
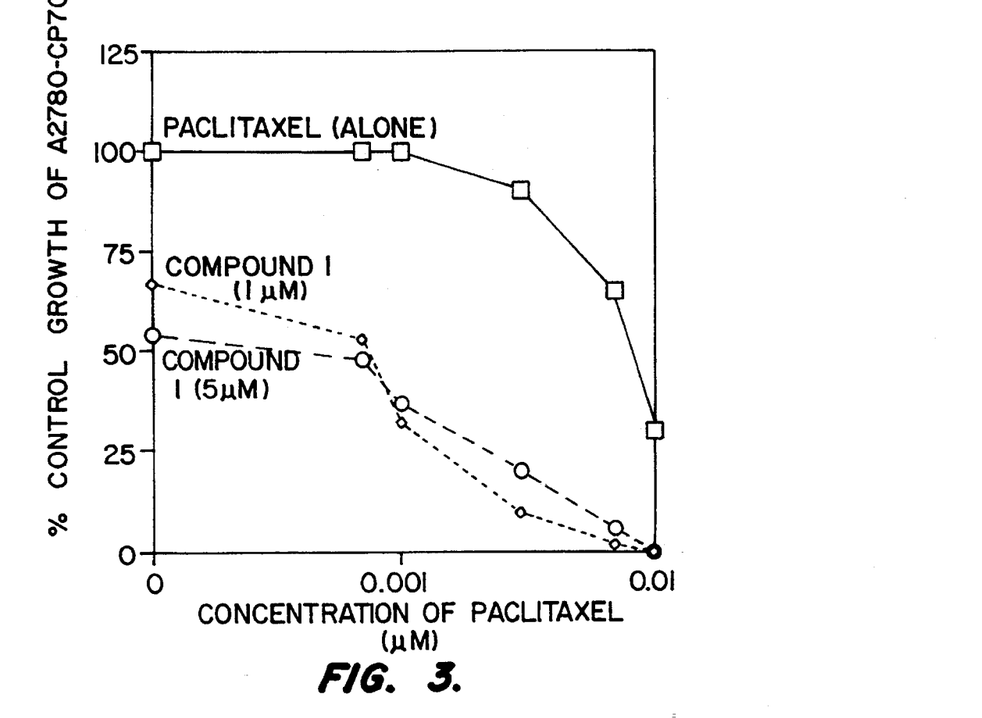
FIG. 3 shows the effect of treating A2780-CP70 cells with compound 1 (at 0, 1 and 5 μM) followed by paclitaxel

Cells were incubated overnight in serum-containing medium, then washed once and treated with compound 1 (0, 1 and 5 μM). After 24 hr, the cells were washed once with PBS and then treated with compound 3 (0 to 0.01 μM) for an additional 24 hr. The resulting cells were washed once with PBS, treated with serum-containing media and incubated for 5 days. The cells were then fixed and stained with methylene blue in 40% methanol and the colonies were counted. FIGS. 2 and 3 show the results for the A2780 and A2780-CP70 cells, respectively. Data are presented as a percent of control (DMSO vehicle) growth. A supra-additive effect was demonstrated with this sequence of drug administration for both cells lines.

EXAMPLE 3

This example illustrates the effect of independently treating A2780 and A2780-CP70 cells with paclitaxel (compound 3) and a subsequent treatment with compound 1.

Figure 4:
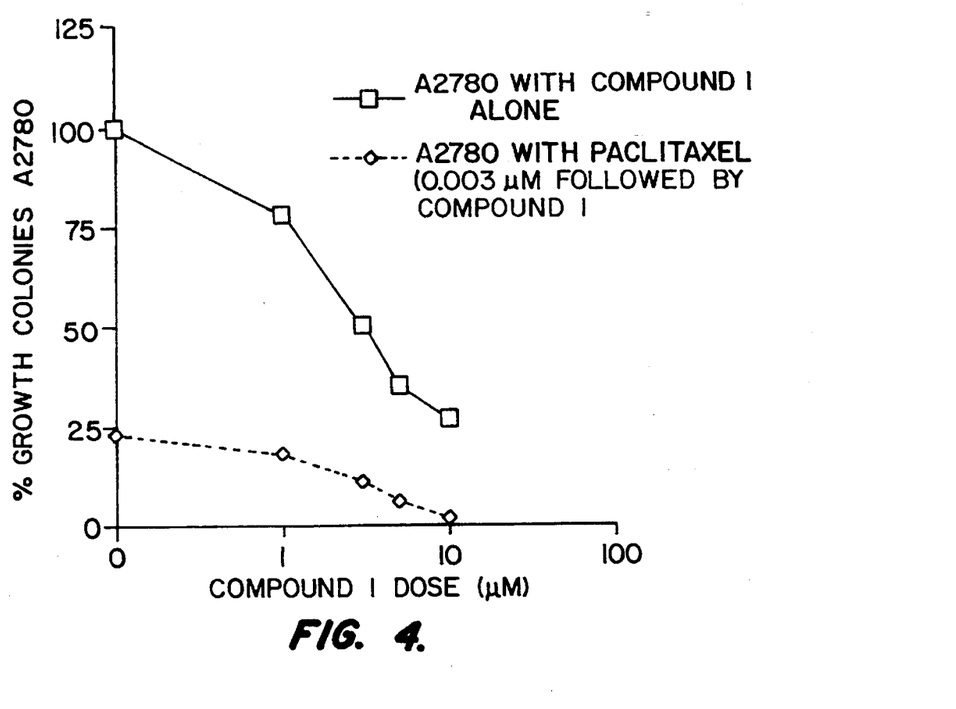
FIG. 4 shows the effect of treating A2780 cells with paclitaxel (0.003 μM) followed by compound 1.
Figure 5:
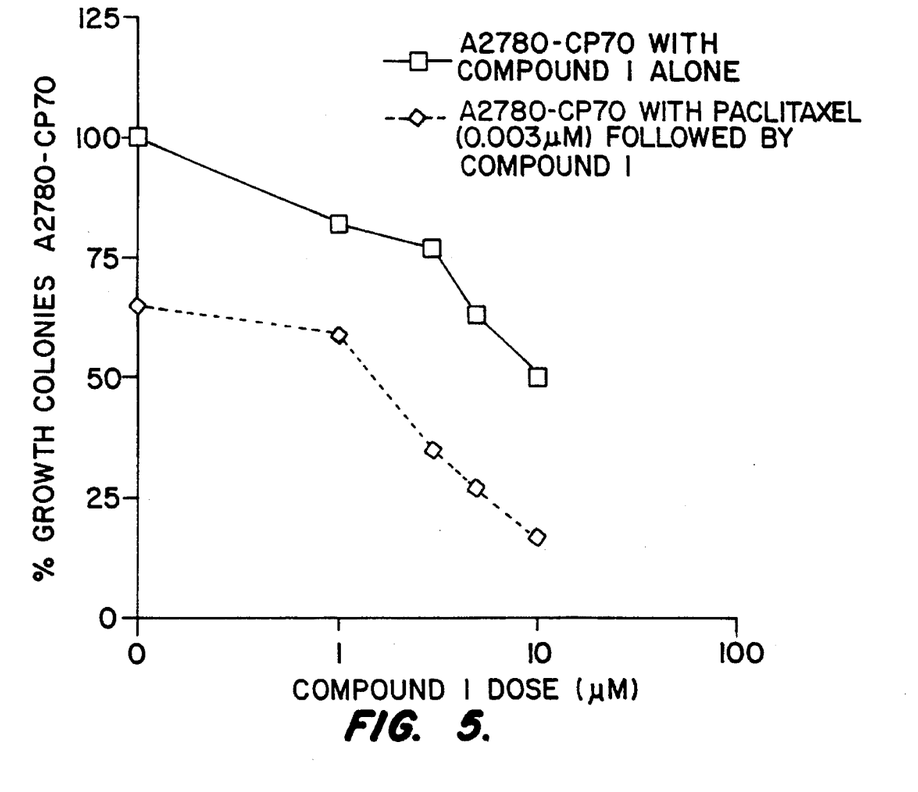
FIG. 5 shows the effect of treating A2780-CP70 cells with paclitaxel (0.003 μM) followed by compound 1.

Cells (A2780 or A2780-CP70) were allowed to incubate overnight then washed once with PBS and treated with paclitaxel at dose ranges of 0 and 0.003 μM for 24 hr. The resulting cultures were washed once with PBS and then treated with compound 1 (0 to 10 μM, see FIGS. 4 and 5) for 24 hr. The cells were again washed with PBS and treated with compound 1 (0 to 10 μM) for 24 hr, washed again with PBS and incubated for 5 days in drug-free media. The resulting cells were fixed, stained and the colonies were counted. Data are presented in FIGS. 4 and 5 as a percentage of control growth (DMSO treatment only). FIG. 5 shows that an additive effect is seen with this sequence of drug administration for the cisplatin-resistant cell line.

EXAMPLE 4

This example illustrates the effect of treating A2780 and A2780-CP70 human ovarian cancer cells and MDA 231 human breast cancer cells with compound 1 followed by paclitaxel (compound 3) in monolayer assays.

Figure 6:
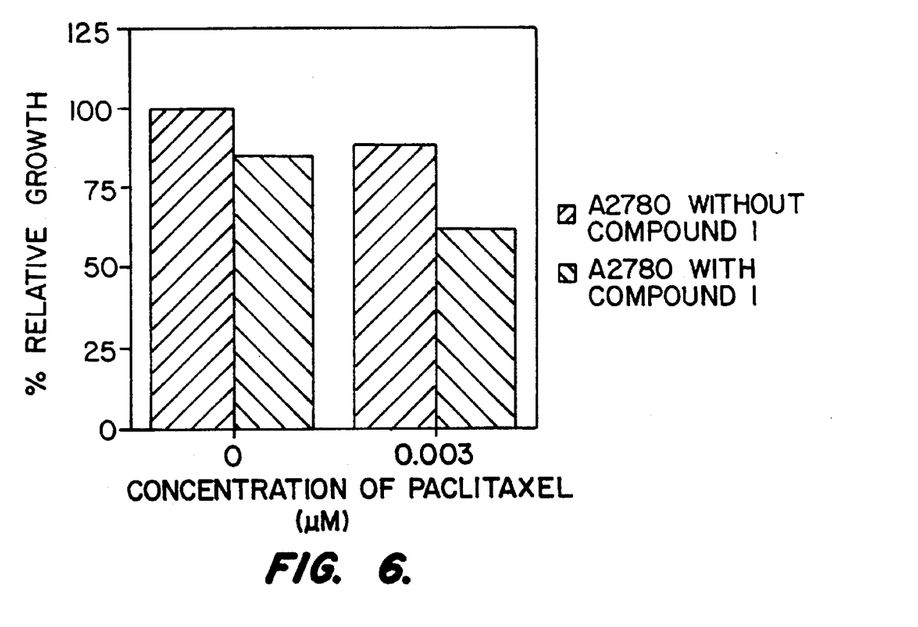
FIGS. 6–8 show the effects of treating A2780 cells, A2780-CP70 cells and MDA231 cells in a monolayer assay with compound 1 (5 μM for 24 hours) followed by paclitaxel (0.003 μM for 24 hours).
Figure 7:
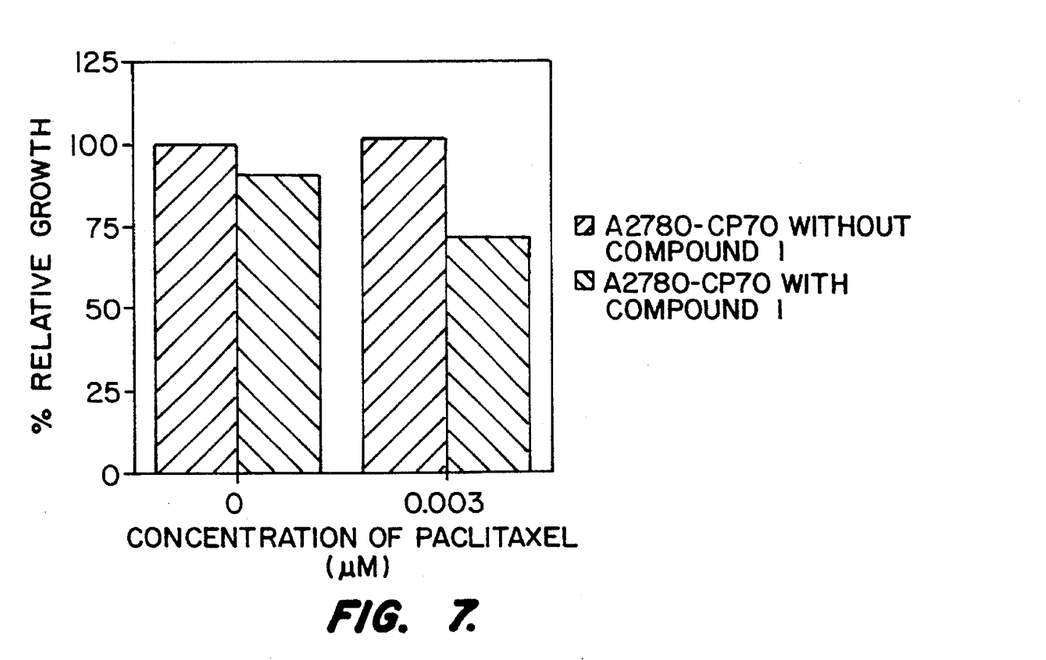
Figure 8:
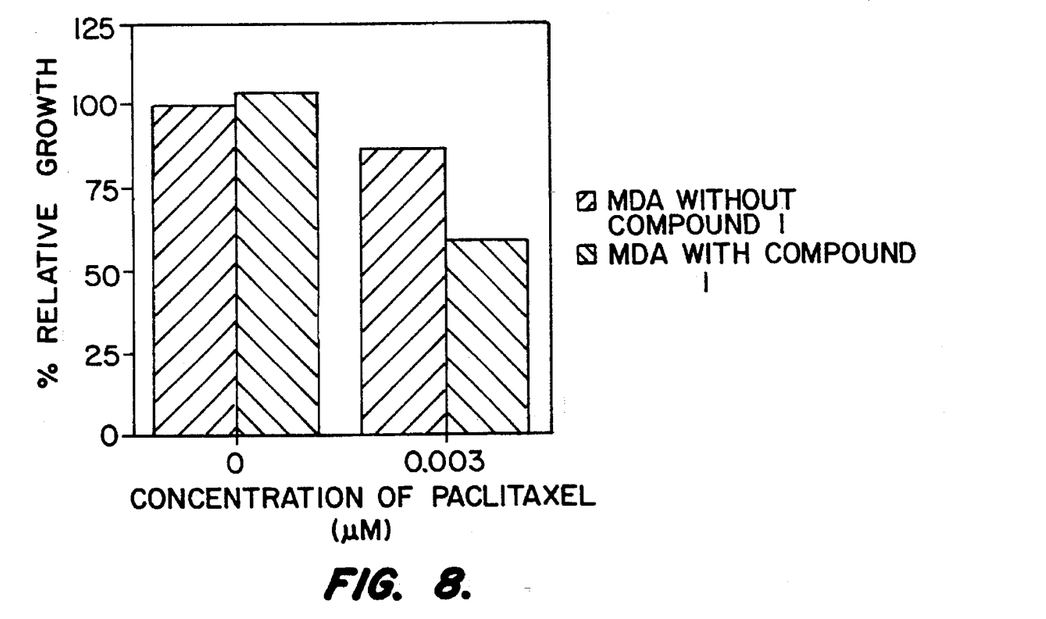

For each of the cell types, 50,000 cells were plated per well in 24-well tissue culture plates. One mL of medium was added to each well and the cells were incubated overnight at 37° C. The media was carefully aspirated away and media (1 mL) containing compound 1 (5 μM) or DMSO vehicle control was added to each well. After incubating the cells for 24 hr at 37° C., the media from each well was carefully aspirated away and each well was washed twice with serum-free media. Media (1 mL) containing paclitaxel (0, 0.001, 0.003, or 0.007 μM) was added to the appropriately labeled wells and the plates were incubated for 24 hr at 37° C. After the incubation, the media was aspirated away and each well was washed twice with serum-free media. Serum-containing media was then added to each well and all plates were incubated for 4 days at 37° C. At the end of 4 days, the media was aspirated off and wells were fixed and stained with crystal violet in methanol. The wells were air dried and eluted with sodium citrate and ethanol. The optical density (OD) was determined for each of the well eluates at 540 nm. The percent relative growth was calculated by dividing the mean OD of identically treated wells by the OD of the control and multiplying by 100. The results are shown in FIGS. 6–8. In all cell lines tested, a supra-additive effect was found for with this sequence of drug administration.

EXAMPLE 5

This example illustrates the effect of treating A2780 and A2780-CP70 cells with compound 1 in combination with carboplatin.

Figure 9:
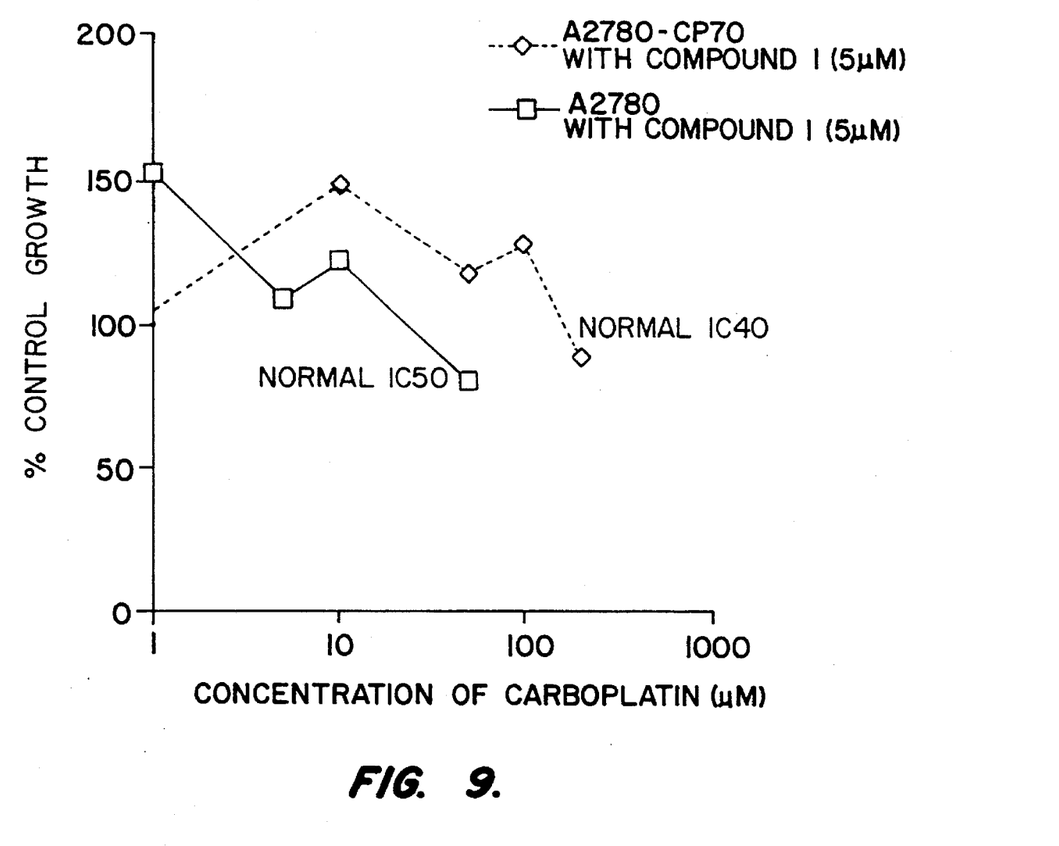
FIG. 9 shows the sub-additive effect of carboplatin with compound 1 on A2780 and A2780-CP70 cells.

Cells were incubated overnight in serum-containing medium, then washed once and treated with compound 1 (5 µM). After 24 hr, the cells were washed once with PBS and then treated with carboplatin (1 to ~200 µM) for an additional 24 hr. The resulting cells were washed once with PBS, treated with serum-containing media and incubated for 5 days. The cells were then fixed and stained with methylene blue in 40% methanol and the colonies were counted. FIG. 9 shows the results for the A2780 and A2780-CP70 cells. Data are presented as a percent of control (DMSO vehicle) growth. A sub-additive effect was demonstrated with this sequence of drug administration for both cells lines. Additionally, when the sequence of drug administration was reversed, a sub-additive effect was still apparent.

EXAMPLE 6

This example illustrates the clinical treatment of a patient having breast cancer.

A patient having breast cancer is selected for treatment. The cancer is diagnosed by appropriate tests such as tissue biopsy with histology studies. A medical history and physical examination are pertbrined with special attention to the neurological examination and to signs of the cancer.

Initial studies are performed, including a complete blood count with a white cell count, differential, and platelet count; an automated chemistry profile (SMAC-20) including levels of sodium, potassium, chlorides, carbon dioxide, blood urea nitrogen (BUN), creatinine, calcium, phosphorus, cholesterol, triglycerides, alkaline phosphatase, lactose dehydrogenase (LDH), serum transaminases (such as SCOT, SGPT, GGT), creatine phosphokinases (CPK), lipase, and amylase; thyroid function tests; an erythrocyte sedimentation rate (ESR); protime and partial thromboplastin time (PT, PTT); a urine analysis and a 24 hour creatinine clearance; a chest X-ray (CXR); and an electrocardiogram (EKG).

Tests for tumor markers are done, such as a carcinoembryonic antigen (CEA) level, as well as tests for tumor location, size, and spread (both local and systemic or metastatic). The latter can include additional X-ray studies, sonograms, computer assisted tomography (CAT scans), magnetic resonance imaging (MRI), positron emission studies (PET scans), and the like.

During the treatment course, studies are repeated as indicated. The neurological examination; and the complete blood count with white cell count, differential, and platelet count are performed at least every three or four days.

On the first day of therapy, compound 1 is given to the patient orally as a solution of PEG 400 at a concentration of 100 mg/mL. The dose is 100 mg/m² of body surface area per day in a single dose. The patient takes nothing by mouth except the compound 1 for three hours before and one hour after the compound I dose. This dose is repeated daily for a total of eight consecutive days.

On the eighth day, two hours after the compound 1 dose, the patient is treated With a single dose of paclitaxel. The paclitaxel is supplied as a concentrated nonaqueous solution of 6 mg/mL in a polyoxylated castor oil 50% and dehydrated alcohol 50% vehicle. The concentrated paclitaxel is diluted with 5 % dextrose solution to a final concentration of 0.3 to 1.2 mg/mL. The paclitaxel, which is given to the patient immediately after final dilution, is administered in polypropylene containers (bags and tubing). The dose of paclitaxel is 200 mg/m² of body surface area.

Access to the patient is by a central venous line, and the paclitaxel solution is infused over about three hours beginning two hours after the compound 1 dose. The patient is closely observed during and for four hours after completion of the infusion, including monitoring of vital signs hourly.

A second cycle of therapy can begin on the twenty-second day, with the first day of compound 1 therapy counting a day one. The procedure is as described above, except that the dose of either or both the compound 1 and paclitaxel can be increased. Typically, the compound 1 dose is held constant, and the paclitaxel dose is increased by about 15 to 50 mg/m².

The invention being thus described it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A pharmaceutical composition comprising, an effective amount of a first compound having formula I:

$$Y-(CH_2)_p-Ar^{11}-X-Ar^{12} \qquad (I)$$

wherein:

is an integer of from 0 to 4;

$Ar^{11}$ and $Ar^{12}$ are each aromatic moieties independently selected from the group consisting of phenyl, naphthyl, halo-substituted phenyl, halo-substituted naphthyl;

X is a linking moiety selected from the group consisting of O, S, $SO_2$, CO, CHCN, straight chain alkyl, alkoxy, and alkoxyalkyl; and Y is a nitrogen-containing heterocyclic moiety of formula II:

wherein:

A is a member selected from the group consisting of N and CH;

$R^1$ is a member selected from the group consisting of hydrogen, $-CONH_2$, $-CONHR^3$, $-CO_2H$, $-CO_2R^3$, and $-SO_2NH_2$, $R^2$ is a member selected from the group consisting of hydrogen, $-NHCOC_6H_5$, $-NH_2$, $-NHR^3$, $-NC(R^3)_2$, $-NHCOR^3$, and $-NH-CHO$; and $R^3$ is lower alkyl of from 1 to 6 carbon atoms, and an effective amount of a second compound selected from the group consisting of paclitaxel, motere, and modified taxane analogs in a pharmaceutically acceptable carrier.

2. A composition in accordance with claim 1 wherein said first compound is 5-amino-1-(4-(4-chlorobenzoyl)-3,5-dichlorobenzyl)- 1,2,3-triazo-4-carboxamide.

3. A composition in accordance with claim 1 wherein said first compound is 5,amino-1-(4-(4-chlorobenzoyl)-3,5-dichlorobenzyl)-1,2,3-triazole-4-carboxamide and said second compound is paclitaxel.

4. A composition in accordance with claim 1 further comprising an antimycotic imidazole selected from the group consisting of ketoconazole, fluconazole, itraconazole, econazole and miconazole.

5. A method for treating cancer in a subject, said cancer being selected from the group consisting of breast cancer, lung cancer, melanoma, and ovarian cancer, said method comprising:

(i) administering to said subject an effective amount of a compound of formula I:

wherein:

p is an integer of from 0 to 4;

$Ar^{11}$ and $Ar^{12}$ are each aromatic moieties independently selected from the group consisting of phenyl, naphthyl, halo-substituted phenyl, halo-substituted naphthyl;

X is a linking moiety selected from the group consisting of O, S, $SO_2$, CO, CHCN, straight chain alkyl, alkoxy, and alkoxyalkyl; and Y is a nitrogen-containing heterocyclic moiety of formula II:

wherein:

A is a member selected from the group consisting of N and CH;

$R^1$ is a member selected from the group consisting of hydrogen, $-CONH_2$, $-CONHR^3$, $-CO_2H$, $-CO_2R^3$, and $-SO_2NH_2$, $R^2$ is a member selected from the group consisting of hydrogen, $-NHCOC_6H_5$, $-NH_2$, $-NHR^3$, $-N(R^3)_2$, $-NHCOR^3$, and $-NHCHO$; and $R^3$ is lower alkyl of from 1 to 6 carbon atoms, and (ii) administering to said subject an effective amount of a second compound selected from the group consisting of paclitaxel, taxotere and modified taxane analogs.

6. A method in accordance with claim 5 wherein step (i) is carded out prior to step (ii).

7. A method in accordance with claim 5 wherein step (ii) is carried out prior to step (i).

8. A method in accordance with claim 5 wherein said effective amount of said compound of step (i) is from the range of from about 50 $mg/m^2$ to about 500 $mg/m^2$ of body surface area of said subject.

9. A method in accordance with claim 5 wherein said effective amount of said compound of step (i) is from the range of from about 50 $mg/m^2$ to about 500 $mg/m^2$ of body surface area of said subject and said effective amount of said compound of step (ii) is selected from the range of from about 75 $mg/m^2$ to about 300 $mg/m^2$ of body surface area of said subject.

10. A method in accordance with claim 5 wherein said subject is human.

11. A method in accordance with claim 5 wherein said subject is human, said compound of step (i) is 5-amino-1-(4-(4-chlorobenzoyl)-3,5-dichlorobenzyl)- 1,2,3-triazole-4-carboxamide and said compound of step (ii) is paclitaxel.

12. A method in accordance with claim 5 wherein said first compound is administered orally.

13. A method in accordance with claim 5 wherein said second compound is administered by intravenous injection.

14. A method in accordance with claim 5 wherein said compounds of steps (i) and (ii) are administered in combination with a compound selected from the group consisting of G-CSF, an antimycotic imidazole, and a mixture thereof.

* * * * *